US006889558B2

(12) United States Patent
Hines

(10) Patent No.: US 6,889,558 B2
(45) Date of Patent: May 10, 2005

(54) REAL-TIME DISPLAY OF INTERNAL GYRATION ANGLE IN GYRATORY COMPACTION MATERIAL TESTING

(75) Inventor: Theodore G. Hines, Grove City, PA (US)

(73) Assignee: Pine INstrument Company, Grove City, PA (US)

( * ) Notice: Subject to any disclaimer, the term of this patent is extended or adjusted under 35 U.S.C. 154(b) by 30 days.

(21) Appl. No.: 10/273,864

(22) Filed: Oct. 18, 2002

(65) Prior Publication Data

US 2003/0075820 A1 Apr. 24, 2003

Related U.S. Application Data

(60) Provisional application No. 60/346,068, filed on Oct. 19, 2001.

(51) Int. Cl.⁷ .................................................. G01N 3/10
(52) U.S. Cl. .......................................... 73/825; 73/818
(58) Field of Search ........................... 73/818, 824, 825, 73/813, 814, 815, 816, 817, 819, 821

(56) References Cited

U.S. PATENT DOCUMENTS

| 5,275,056 A | * | 1/1994 | Hamilton et al. | .............. 73/794 |
| 5,824,913 A | * | 10/1998 | Pyle | ............................ 73/818 |
| 5,911,164 A | * | 6/1999 | McRae | ........................ 73/815 |
| 6,477,783 B1 | | 11/2002 | Harman et al. | |

FOREIGN PATENT DOCUMENTS

EP          1348942 A2 * 10/2003    ............ G01N/3/56

OTHER PUBLICATIONS

"Application of Internal Angle Verificatio to Obtain Equivalent Results from Various SGC Models", 2001 Pine Instrument Company. Pp. 1–9.

Buchanan, Shane M., et al. "Effect of Superpave Gyratory Compactor Type on Compacted Hot Mix Asphalt (HMA) Density". 2001. Pp. 1–23.

"Economic Impact Refining the Dynamic Internal Angle of the Superpave Gyratory Compactor", SGCEconoImpact_v1.5.doct. Version 1.5, Jan. 29, 2003. Pp. 1–10.

"Troxler's Superpave Gyratory Compactor Operational Specifications", Feb. 2001. Pp. 5.

"Investigating Measurable Gmb Differences Among Gyratory Compacted Specimens A Round Robin Study", May 2001. Pp. 1–9.

"Consideration of Mold Temperature When Measuring the Angle of Gyration on the Troxler Model 4140", Oct. 2001. Pp. 1–6.

"Measuring the Angle of Gyration on the Troxler Superpave Gyratory Compactor–SGC Using an Internal Angle Measuring Device", pp. 1–4.

(Continued)

*Primary Examiner*—Max Noori
(74) *Attorney, Agent, or Firm*—Roetzel & Andress

(57) ABSTRACT

A gyratory compacting apparatus and data capture and display system for compacting a specimen of material within a mold as the mold is gyrated, and capturing and displaying data on an internal angle of gyration during mold gyration, the apparatus and system having a generally cylindrical mold for holding a specimen of material to be compacted, at least one plate in the mold in contact with material in the mold and which moves relative to the mold as the mold is gyrated, and at least one sensor which measures an internal angle of gyration between the mold and a mold plate and captures internal gyration angle data for real-time display of internal gyration angle data during gyration and compaction. Alternative arrays of internal gyration angle sensors are disclosed.

31 Claims, 5 Drawing Sheets

OTHER PUBLICATIONS

"Model 3190 True Mold Angle Device for the Model 4140 Gyratory Compactor", Manual of Operation and Instruction, Edition 1.0, Feb. 2002, pp. 1–20.

"Model 3191 True Mold angel Device for the Model 4141 Gyratory Compactor", Manual of Operation and Instruction, Edition 1.0, Feb. 2002, pp. 1–16.

"Superpave Asphalt Mixture Design Gyratory Compactor Calibration", FHWA updated Apr. 4, 2001. Pp. 1–2.

Schiebel, Bill. "CDOT and Colorado Paving Industry's Actio Plan to Address Recently Documented Issue with Compaction Angle when Using the Troxler Gyratory with Four–Inch Molds". CDOT Asphalt Pavement Program. Apr. 19, 2002. Pp. 1–14.

Harman, Thomas. Letter about CDOT and Colorado Paving Industry's Action Plan. Apr. 10, 2002. Pp. 1–3.

Harman, Thomas. Letter about CDOT and Colorado Paving Industry's Action Plan. Apr. 9, 2002. Pp. 1–2.

"Superpave Gyratory Validation Kit Manufacturer's Meeting". FHWA Meeting Minutes (FINAL).doc Jan. 29, 2003 revised and amended Sep. 8, 2000. Pp. 1–7.

"Standard Practice for the Evaluation of the Superpave Gyratory compactor's (SGC's) Angle of Gyration using hte FHWA SGC Angle Validation Kit". Pp. 1–7.

"Observations of SGC End Plate Deflection Using the FHWA Angle Validation Kit", 2000 Pine Instrument Company. Pp. 1–15.

"Superpave Gyratory Compactors—Angle Sensitivity", 2000 Pine Instrument Company. Pp. 1–9.

"Investigation of Pine Superpave Gyratory Compactors Using the FHWA Angle Validation Kit", 2000 Pine Instrument Company. Pp. 1–8.

* cited by examiner

US 6,889,558 B2

REAL-TIME DISPLAY OF INTERNAL GYRATION ANGLE IN GYRATORY COMPACTION MATERIAL TESTING

This application claims the benefit of Provisional Application No. 60/346,068, filed Oct. 19, 2001.

FIELD OF THE INVENTION

The present invention relates generally to a method and apparatus for testing materials and, in particular, to a method and apparatus for testing materials by simultaneous compaction and gyration, and real-time collection and presentation, transfer or display of data from such tests.

BACKGROUND OF THE INVENTION

Gyratory compactors are used to test material properties, such as hot-mix asphalt (HMA) mixture specimens in the laboratory to assess and predict paving material performance. For HMA testing, Federal Highway Administration (FHWA) guidelines and test procedures require in essence that an asphalt material sample be gyrated within a mold while undergoing compaction, to simulate the effect of road traffic. The extent of compaction according to the testing procedures is controlled by the force applied to a compaction ram, the angle of gyration or orbiting of a cylindrical mold which holds a material specimen "gyration angle", and the number of gyrations. The angular extent of gyration is determined by an angle of the mold relative to the axis of the compaction ram. Precise dynamic measurement of the gyration angle is critical to achieve accurate test results, and is complicated by the constant gyration/orbiting motion of the mold as material is compacted within it.

Gyratory compactor machines typically include a cylindrical material holding mold which is gyrated by a gyration mechanism and positioned for insertion of a ram into the mold cavity to compress the material in the mold as the mold is gyrated. Representative gyratory compactor machines include those manufactured by Pine Instrument Company and described in U.S. Pat. Nos. 5,456,118; 5,606,133; 5,824,913 and 5,817,946, and other types of such machines which perform these functions. The material-holding mold may be gyrated about a small angle relative to the vertical axis of the ram (the gyration angle), by orbiting one end of an axis of the mold as the material is compressed within the mold by the ram to simulate actual forces on the material in the application environment. Specimens of a consistent density are produced when a gyratory compactor maintains a constant pressure and a known constant angle of gyration during the compaction process. Inconsistencies in asphalt specimens produced on different gyratory compactor models have been attributed to variations in the angle of gyration.

Some gyratory compactors measure the angle of gyration by referencing the external cylindrical mold wall to a reference frame, such as a vertically oriented member of the compactor machine frame. However, the asphalt mixture being compacted is contained on the inside of the mold, being compressed by mold end plates, pucks and/or ram heads. It is the angle between the mold cylinder and these internal compaction surfaces of the end plates that determines the amount of compaction effort imparted onto the HMA specimen. This angle, referred to herein alternatively as the "internal angle", "internal angle of gyration", or "internal mold gyration angle", must be accurately maintained throughout a gyratory compaction test procedure in order to achieve the proper degree of compaction and accurate test results. It is therefore important to have information regarding the internal gyration angle for each test. A typical gyratory compactor utilizes a mold comprising of a mold body of substantially cylindrical shape, referred to herein as the mold cylinder, and at least one end plate, but preferably two end plates. In such a compactor, there are actually two internal angles of gyration, one at each end of the asphalt specimen. The internal angle of gyration is measured at each end of the asphalt specimen and the average of the two measurements is used to establish the effective internal angle. Although the internal angles at each end of the specimen are of interest, it is the effective internal angle of gyration that is of primary interest.

Measurement and display of the internal angle of gyration, vital to obtaining accurate tests results, is a feature not adequately addressed in the design of prior art gyratory compactors. In prior art gyratory compactors, when operated without an internal angle measurement device, the gyration angle is set prior to running a test on a material specimen. It is then simply assumed that the machine maintains this angle throughout the test operation. It is further assumed that the test results are based upon the pre-set gyration angle being maintained throughout the gyratory compaction process. Machines which do not maintain the internal angle of gyration in operation produce inaccurate test results.

There has been developed a device which measures the internal angle of gyration, by placing within the mold at least two probes which contact the inner mold wall. The data retrieved from the probes, along with the known spacing between the probes, is used to calculate the internal angle of gyration with respect to the mold base plate or top plate. The instrument interfaces with a computer through cable connection to setup the data collection parameters and to retrieve the data once the compaction test is complete. The instrument does not provide or display internal gyration angle data during the compaction test, which would allow a machine operator to immediately tell whether a particular test was being performed within the specified parameters. Furthermore, the use of this separate angle validation device requires separate insertion of the device into a gyratory compactor in order to conduct a test from which angle data can be acquired.

SUMMARY OF INVENTION

The present invention provides an improved apparatus and method for performing material testing by gyratory compaction wherein the angle of gyration, including the internal angle of gyration, is precisely measured and presented or displayed during and throughout the entire testing process. In accordance with one aspect of the invention, a materials testing apparatus for subjecting a material to forces is provided which measures and displays an internal angle of gyration to which material is subjected during the testing process. The apparatus includes a mold for containing a quantity of material, a material compaction ram for exerting a compressive force upon material while the mold is gyrated relative to the axis of compression of the ram, one or more sensors operative to determine an angle of gyration of the mold, and a display or other data transfer or presentation system for indicating an internal angle of gyration of the mold or other test parameters as the mold is gyrated.

In accordance with another aspect of the invention, there is provided a gyratory compactor apparatus for subjecting a material to forces and measuring and displaying parameters of the forces while the forces are applied to the material. The gyratory compactor apparatus includes a mold for receiving a quantity of material, a ram inserted into the mold against the material in the mold, a mechanical system for gyrating the mold while the ram is inserted into the mold, a sensor for sensing a gyration angle of the mold, and a display for displaying an internal angle of gyration of the mold as the mold is gyrated.

In accordance with another aspect of the invention, a gyratory compactor apparatus for subjecting a material to forces is provided which includes a system for determining and displaying an internal angle of gyration. In an alternate embodiment of the invention, a self-contained angle measurement instrument is placed into the compaction mold along with the asphalt mixture. The angle measurement instrument contains one or more sensors which measure the angle between a mold end plate (also referred to as a "mold plate") and an interior of the mold cylinder. The measured internal gyration angle is then compared to a measured external mold cylinder angle (measured by sensing a position of an exterior of the mold cylinder), which is measured separately with respect to a secondary frame of reference. The difference between the readings is calculated and the result is applied to the mold cylinder measurement as an offset compensation factor. As the compactor operates, the mold cylinder angle is measured and the offset compensation factor is applied to determine the internal angle of gyration. The compensated internal angle measurement is displayed to the operator while the material is compacted. This alternate method of obtaining the internal gyration angle value from a self-contained, separate instrument and applying an offset compensation factor to the externally measured mold cylinder angle has the advantage of not requiring the use of any delicate measuring instruments inside the compaction mold under normal operating situations. Any of the measured angles or other data can be displayed separately or in combination in a display associated with a gyratory compactor.

In an alternate embodiment, the internal angle is measured at both mold end plates then averaged This average internal angle is compared to the mold cylinder measurement and a compensation factor is calculated. The compensation value is then applied to the mold cylinder measurement while the material is compacted and an internal angle of gyration is presented to the operator.

An alternate method and system of the invention to obtain the internal angle of gyration is to instrument the gyratory compactor to directly measure at least one of the mold end plates with respect to a reference frame. The compactor is also instrumented with sensors to measure the mold cylinder angle with respect to the same reference frame. The internal angle and the external angle measurements are combined to yield the internal angle of gyration. This method has the advantage of directly measuring the mold end plate orientation during normal operation.

In accordance with another aspect of the invention, a gyratory compaction apparatus for subjecting a material to forces is provided which includes a method for determining the internal angle of a gyration compactor based on measurement of the external angle of gyration, and presenting said internal angle to the operator. Regardless of the various instrumentation or sensors used to measure the internal angle of gyration, the external angle can be measured in ways similar to existing designs where multiple sensors sense a position of the external mold wall and the angle of gyration is determined. The internal angle of gyration can be measured with multiple probes protruding through the ram heads and/or mold pucks or mold end plates to directly measure the position of the mold end plates during compaction. To reduce the sensitivity to debris, non-contact sensors may be employed in lieu of direct contact style. Angle data is displayed during operation of the gyratory compactor while the compaction is taking place. Angle data can also be printed or saved to a data file for later reference.

DETAILED DESCRIPTION OF PREFERRED AND ALTERNATE EMBODIMENTS

Figure 1:
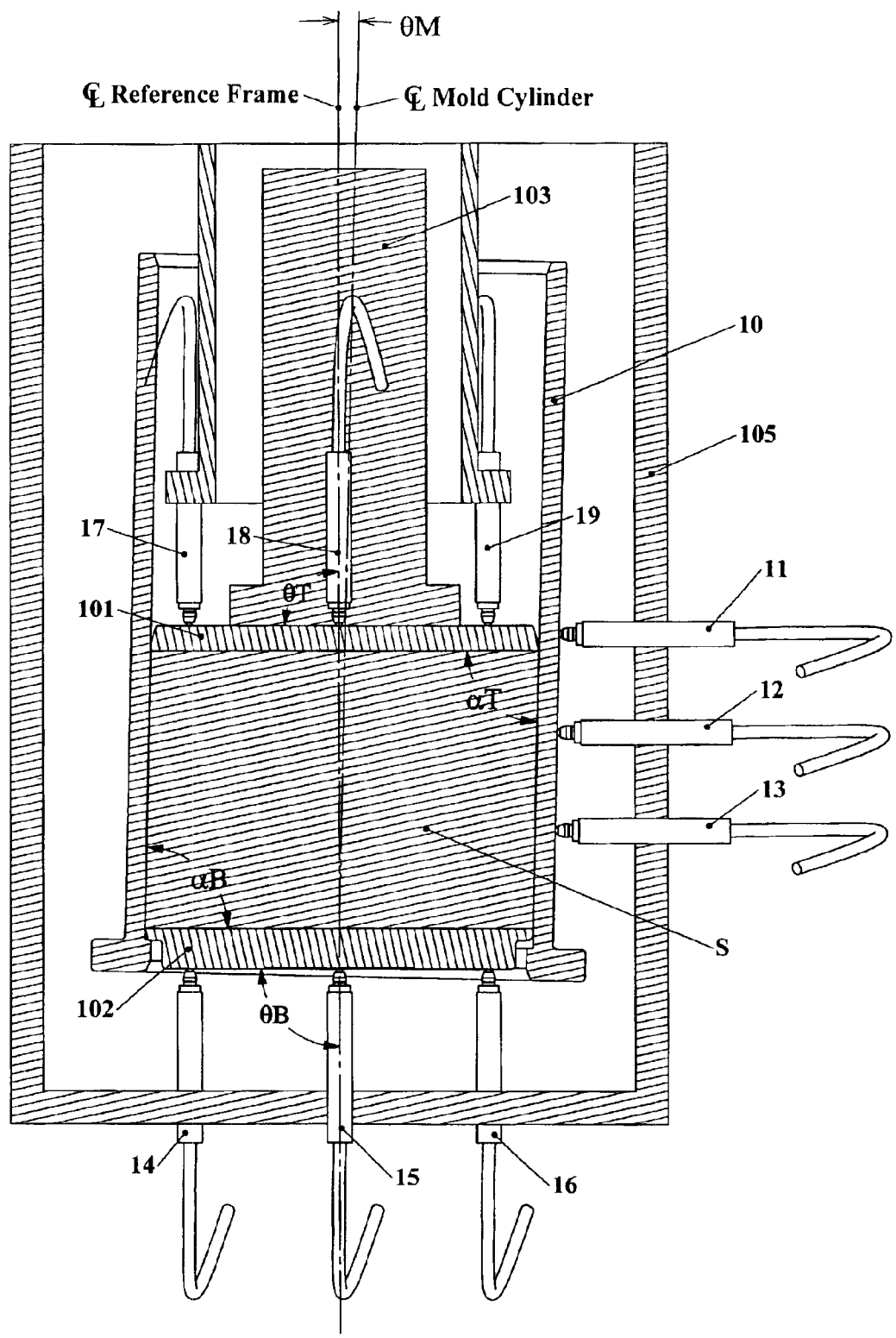
FIG. 1 is a cross-sectional elevation of a gyratory compaction mold containing a material specimen, mold cylinder, mold end plates, and a compaction ram, and a representative gyration angle sensor array.
Figure 2:
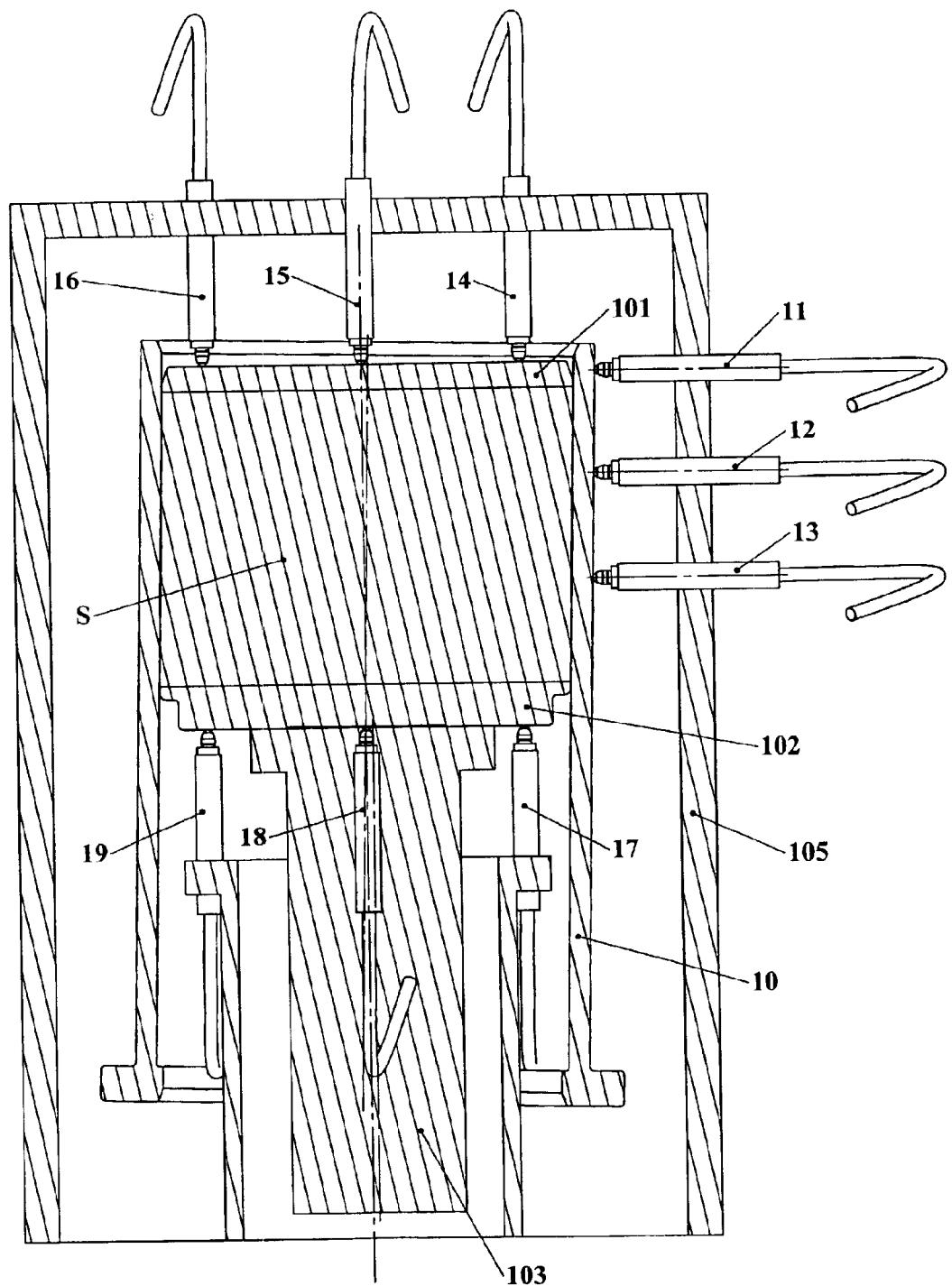
FIG. 2 is a cross-sectional elevation of a gyratory compaction mold containing a material specimen, mold cylinder, mold end plates, and a compaction ram, and an alternative gyration angle sensor array.

FIG. 1 illustrates a mold cylinder 10 of the type commonly used in a gyratory compactor. Within the mold cylinder 10 is positioned a first mold plate 101 and a second mold plate 102, between which a material specimen S such as HMA is placed and compacted by a compaction ram 103 which passes through one end of the mold. A gyratory compactor machine typically has a frame 105 for, among other things, supporting the mold in a generally vertical orientation, a gyration mechanism which engages or moves the mold to gyrate it about its axis, i.e., to move one end of an axis of the mold cylinder in a circle while the opposite end of the axis is held substantially at one point; and a ram 103 (also referred to as a "compaction ram") which is advanced or driven through one of the ends of the mold cylinder 10 against one of the mold end plates 101 or 102 (as shown, against mold plate 101). Alternatively, the ram 103 may have a material contacting surface which contacts the material specimen S directly without a mold plate between the material specimen S and the ram 103.

The mold cylinder 10 is gyrated, i.e., one end of an axis of the mold cylinder, such as the longitudinal axis, is moved throughout a radius while the opposite end of the same axis is held at substantially the same point, by any suitable gyration mechanism, such as known to those of ordinary skill in the relevant art, and as described in the patents cited and disclosed in connection with this patent. In general, mold gyratory mechanisms include those which engage a portion of the mold cylinder, such as the mold wall or a flange which extends from or surrounds the mold cylinder, in order to move the mold in a gyrating or orbiting motion, and those which otherwise displace the mold cylinder from an axis of compression of a ram inserted into the mold through an eccentric device which is rotationally driven to impart gyratory motion to the mold. Other gyratory mechanisms are known to move the mold end plates while holding the mold cylinder substantially stationary to create the gyratory action, i.e., to gyrate material within the mold. All such mechanisms, including all gyratory compactors of the prior art are included within the meanings of the terms "mold gyrator" and "mold gyration mechanism" as used herein.

To the extent the specimen does not occupy all of the internal volume of the mold, that is the end plates 101 or 102 are spaced from the open ends of the mold cylinder, this provides an area internal to the mold but apart from the specimen wherein the described internal gyration angle, i.e., the angles between mold plates 101 and 102 and mold cylinder 10, as depicted by the angles αT and αB, can be accurately measured by the described sensor or by an angle measurement device. An internal mold gyration angle can also be sensed or measured by sensors located substantially outside of the mold cylinder 10, as for example with reference to mold plate 102, which may be at or near the bottom of the mold cylinder 10 or otherwise exposed to an end of the mold cylinder 10, and which is in contact with the material specimen S within the mold. The real-time display of this measured internal angle provides the machine operator with an immediate indication of whether the test is being performed within the defined parameter of the pre-set angle of gyration.

In the embodiment of FIG. 1, external mold cylinder position sensors 11, 12 and 13 (together forming a "sensor array") sense and provide position signal data for display on the position of the mold cylinder relative to a reference frame (angle θM), such as a vertical member of frame 105, or the vertical axis of the compaction ram 103. Sensors 14, 15 and 16 (together forming a sensor array) sense and provide position signal data on the end plate 102, which is compared to the data from sensors 11–13, or to a frame centerline reference, angle θB, to determine an internal gyration angle with respect to end plate 102. Sensors 17, 18 and 19 (together forming a sensor array) sense and provide position signal data on the position of end plate 101, which is compared to the data from sensors 11–13, or to a frame centerline reference, angle θT, to determine the internal gyration angle with respect to end plate 101, and to the compared data from sensors 14–16 to determine an effective internal gyration angle for real-time or near real-time display.

Each of the sensors or sensor arrays may be integrally mounted with the respective components of the machine, while allowing for installation and removal of the mold cylinder 10 or removal of a mold specimen S from the mold cylinder 10. For example, sensors 17–19 may be mounted to move with the end plate 101, or be attached to or installed through the ram 103 for contact with end plate 101 or direct contact with material in the mold cylinder. Sensors which operate other than by direct physical contact may also be employed to carry out the invention. In this patent, a sensor or sensors which determine position or orientation of a machine component such as a mold cylinder or mold plate is operative to sense a position or orientation of such component.

Any type of display may be used to convey gyration angle data during operation of the machine. For example, without limitation, a display may be in the form of a computer screen display generated by software which presents data acquired from the sensor or sensors in graphical or alpha-numeric formats. The display may alternatively be a liquid crystal or LED device which displays a number representing a gyration angle or internal gyration angle in degrees or other units, and which is associated with, electronically connected to, or integrated into a gyratory compactor machine. Alternatively, a graphical display which creates an image representing gyration of the mold within or outside of test parameters. Another form of display may simply be an indicator, such as an indicator light, which when illuminated indicates that a certain test parameter has been met or violated, such as a pre-set or desired angle of gyration. Any other type of real-time or near real-time indication of operation of the gyratory compactor with respect to material test parameters is within the scope of the invention.

Figure 3:
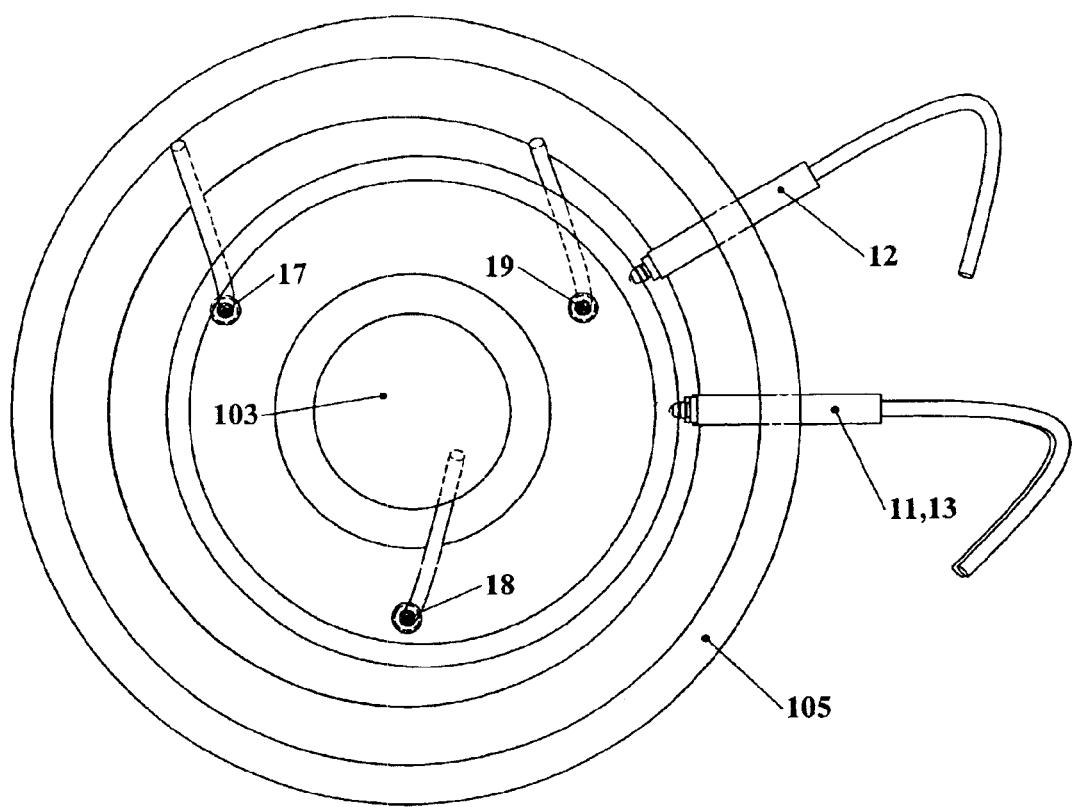
FIG. 3 is an end view of a mold of a gyratory compactor which is instrumented with sensors for sensing a mold gyration angle.

FIG. 3 is a top view of the gyratory compactor components shown in FIG. 1, including frame 105 and mold cylinder 10. In FIG. 3, sensors 17, 18 and 19 are shown in a radial arrangement about mold plate 102. This radial arrangement, e.g., 120 degree spacing, of a three-sensor array enables fully accurate sensing of each complete gyration cycle which, if performed correctly, should result in equal displacement of the mold end plate at each sensor of the array. The use of three sensors (rather than for example one or two sensors) also enables the detection of an elliptical gyration pattern, which may be unacceptable under certain test parameters. Mold cylinder sensors 11, 12 and 13 are also positioned in a triangular or radially spaced array to accurately sense displacement of the mold cylinder relative to a fixed reference, including detection of possible elliptical gyration patterns.

Figure 4:
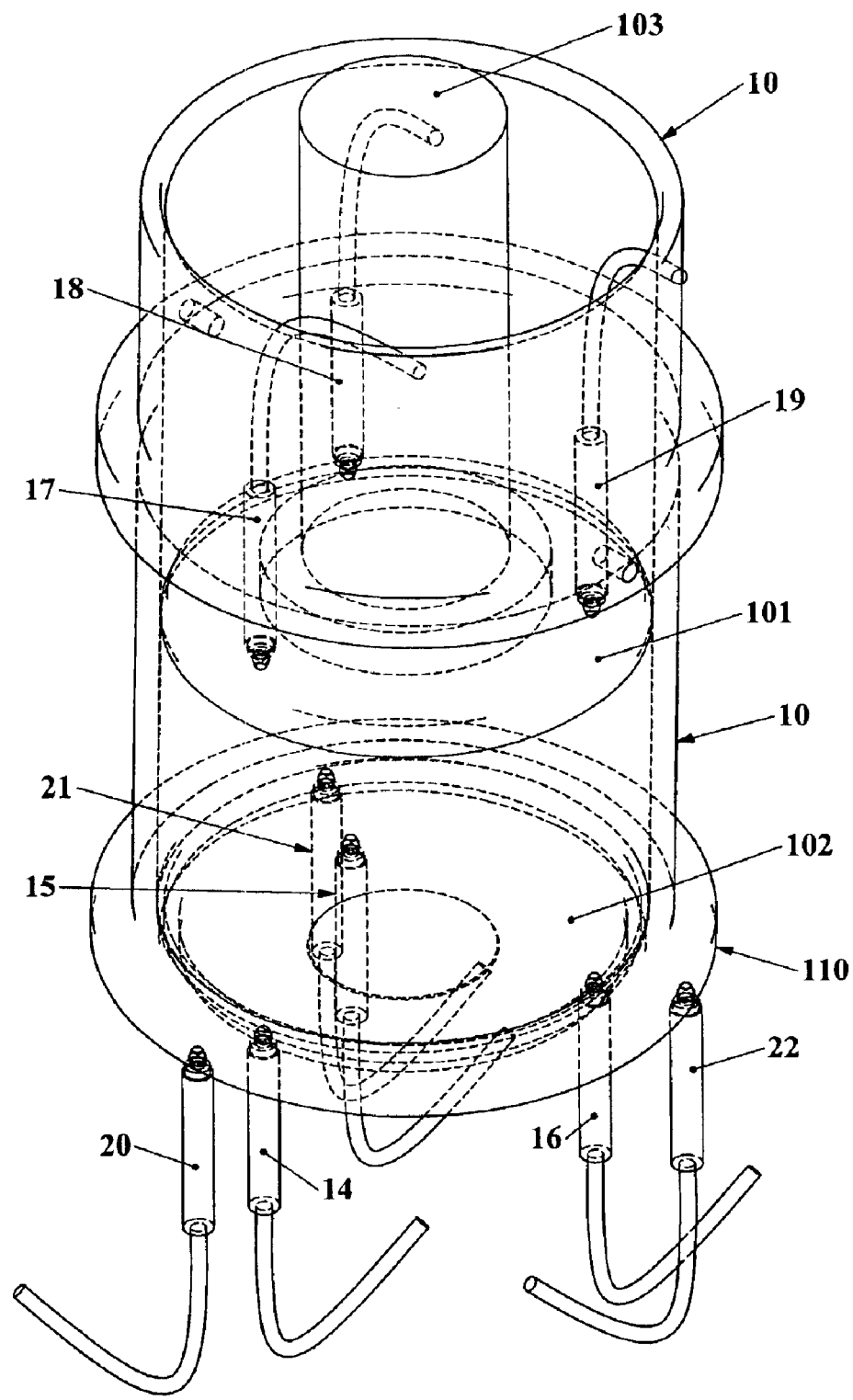
FIG. 4 is a perspective view of a mold of a type used in a gyratory compactor in combination with sensors for sensing a mold gyration angle in accordance with the invention.

FIG. 4 illustrates radial sensor arrays in operative contact with an upper mold end plate 101 (sensors 17, 18 and 19) and lower mold end plate 102 (sensors 14, 15 and 16). Mold cylinder position sensors 20, 21 and 22 are positioned to contact or otherwise operate on or sense a position or orientation of either an end or edge of the mold cylinder or a flange 110 which extends from the mold cylinder. A sensor or sensors operative to sense a position or orientation of the mold cylinder 10 can operate on any area of the mold, such as the interior or exterior of mold wall or walls, terminal ends or edges of the walls or mold, or flanges or other structures which extend from or are attached to the mold cylinder.

Figure 5:
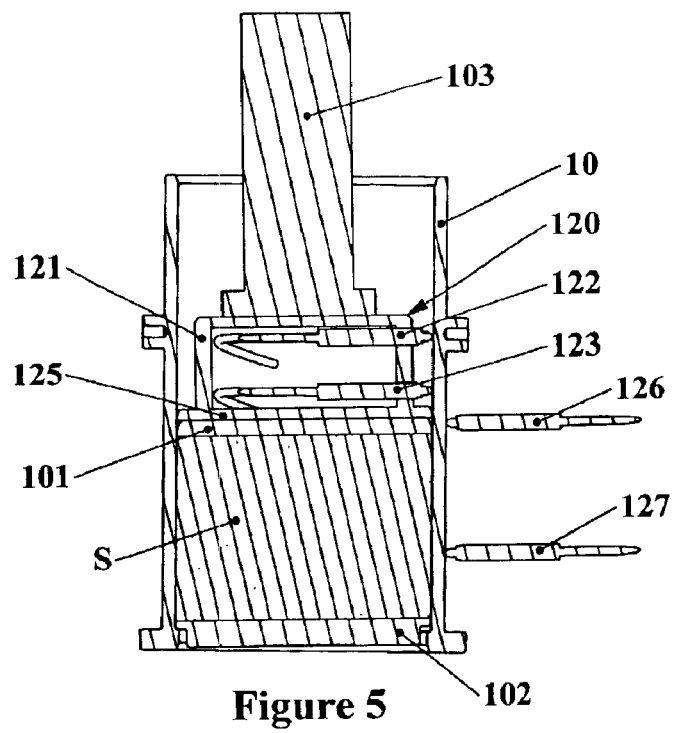
FIG. 5 is a cross-sectional elevation of a gyratory compaction mold containing a material specimen, mold cylinder, mold end plates, and a compaction ram and a gyration angle sensing device proximate to an upper mold end plate.

FIG. 5 illustrates an alternate embodiment of the invention of a gyratory compactor instrumented for real-time internal gyration angle sensing with a substantially self-contained angle measurement device 120 within a housing 121. Internal gyration angle sensors 122 and 123 are positioned within housing 121 to be oriented generally transverse to a vertical axis of mold cylinder 10 to contact the interior surface of the wall of mold cylinder 10. In this particular installation, the housing 121 of the device 120 is located between the compaction ram 103 and the mold end plate 101. An alternative installation is described with reference to FIG. 6. A base 125 of housing 121 is positioned flush against mold plate 101 which is flush against the material specimen S, providing a frame of reference for sensor 122, 123 mounted within the housing 121. The internal angle detection device 120 is preferably hard-wired or wirelessly connected to relay mold cylinder positional data during gyration of the mold in a test operation. External mold cylinder position sensors 126, 127 can be used to compare an external gyration angle to an internal gyration angle sensed by the device 120 to determine a compensation factor for subsequent external angle measurements. However, external sensors 126, 127 are not necessary in the case where the internal angle measurement device 120 is configured to provide real-time data during operation of the machine. The internal sensors 122 and 123 may be used to calibrate the external mold cylinder sensors 126 and 127, which are then utilized throughout the testing procedure.

Figure 6:
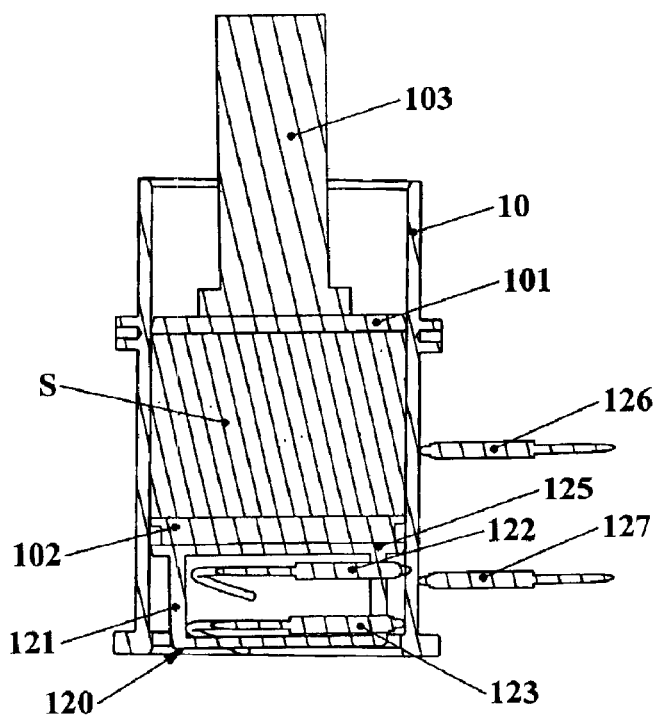
FIG. 6 is a cross-sectional elevation of a gyratory compaction mold containing a material specimen, mold cylinder, mold end plates, and a compaction ram and a gyration angle sensing device proximate to a lower mold end plate.

As shown in FIG. 6, the described internal gyration angle measurement device 120 may be inserted within a gyratory compactor proximate to a lower mold plate 102, e.g., opposite ram 103, and similarly electronically configured as described above to generate gyration angle data throughout a test procedure, which data is displayed, presented, transferred or otherwise made available during and/or throughout the test procedure. As described above, with the internal gyration angle measurement device 120 suitable electronically configured (e.g., via wired or wireless connection) to a data collection and presentation/display system to provide real-time angle data, external mold cylinder position sensors (e.g., sensors 126, 127) are not required for internal gyration angle sensing.

Any type of suitable position or motion sensors may be used in accordance with the invention, including optical sensors. More preferably, fewer or a single sensor may be used in place of a sensor array (such as internal sensors 17, 18) to determine in real-time the position of the mold cylinder relative to one or both of the end plates. Alternatively, a sensor array which provides data on the position of the axis of the mold cylinder relative to an axis of a linearly guided compaction ram can be employed to determine internal angles of gyration during testing.

Each sensor of the described systems is preferably operatively coupled to appropriate signal processing electronics, which may be interfaced with a gyratory compactor control system, or separately connected to a data collection and display, such as a programmed CPU with a display, the display being programmed to provide a graphic or alpha-numeric indication of an internal angle of gyration while the gyratory compactor is in operation. Alternately, the internal angle of gyration can be displayed as part of a report generated by the programmed CPU after the compaction sequence is complete or printed directly from the compaction apparatus. This report also may be in a graphic or alpha-numeric format.

Although the invention has been shown and described with respect to certain preferred embodiments, certain variations and modifications may occur to those skilled in the art. The invention is not limited to any one type of gyratory compactor or material testing device, any one type of motion or position sensor, or any one type of data capture and presentation or display. All such variations and modifications of the apparatus and method are within the scope of the present invention as defined by the accompanying claims and equivalents thereof.

What is claimed is:

1. A gyratory compactor apparatus for compacting a material held in a mold as the mold is gyrated, the apparatus comprising:
   a mold for receiving material to be compacted;
   a ram for compacting material in the mold by insertion of the ram into the mold;
   a mold gyrator for gyrating the mold as the compaction ram is insert into the mold against the material;
   a sensor for sensing a mold gyration angle, and
   a display electrically connected to the sensor for presenting internal angle of gyration information from the sensor as the mold is gyrated by the gyratory compactor apparatus.

2. A method of measuring and displaying an internal angle of gyration in a gyratory compactor device having a material holding mold, which is mechanically gyrated, and at least one mold plate in contact with material in the mold, the mold plate being able to move relative to the mold cylinder as the mold is gyrated, the method comprising the steps of:
   providing a sensor which senses an angular orientation of the mold cylinder relative to a reference frame as the mold is gyrated, a means to provide a compensation factor indicative of the difference between the sensor output and the internal angle of gyration as the mold is gyrated, and displaying information from the sensor indicative of an internal angle of gyration as the mold is gyrated.

3. The gyratory compactor apparatus of claim 1 wherein the sensor comprises at least one sensor which senses a position of the mold cylinder with reference to a fixed portion of the gyratory compactor apparatus.

4. The gyratory compactor apparatus of claim 1 further comprising a mold plate which fits within the mold cylinder and is in contact with material in the mold, and wherein the sensor for presenting mold internal angle of gyration information comprises at least one sensor which senses a position of the mold cylinder with reference to a fixed portion of the gyratory compactor apparatus, and at least one sensor which senses a position of the mold plate within the mold.

5. The gyratory compactor apparatus of claim 1 wherein the sensor for sensing an internal mold gyration angle comprises an array of three sensors operative to sense a position of the mold cylinder.

6. The gyratory compactor apparatus of claim 1 wherein the sensor for sensing a mold gyration angle comprises an array of three sensors for sensing a position of the mold cylinder, and an array of three sensors for sensing a position of an end of the material in the mold.

7. The gyratory compactor apparatus of claim 1 wherein the sensor for sensing a mold gyration angle senses a position of mold plate within the mold.

8. The gyratory compactor apparatus of claim 1 wherein the sensor for sensing a mold gyration angle senses a position of the ram in the mold.

9. The gyratory compactor apparatus of claim 1 wherein the sensor for sensing a mold gyration angle comprises at least one sensor which senses a position of first mold plate within the mold, and at least one additional sensor, which senses a position of a second mold plate within the mold, and at least one mold cylinder sensor which senses a position of the mold cylinder.

10. The gyratory compactor of claim 1 wherein the sensor for sensing a mold gyration angle comprises at least one sensor within a housing positioned at least partially within the mold.

11. The gyratory compactor apparatus of claim 1 wherein the display indicates information on an internal angle of gyration in combination with information on a desired internal angle of gyration.

12. A gyratory compactor apparatus for testing material by compacting material in a mold and simultaneously gyrating the mold, the apparatus comprising:
   a mold for holding material, a material compacting ram, and a mold gyrator,
   a sensor operative to sense an angle of gyration of the mold, and
   a display for displaying information on an internal angle of gyration of the mold as the mold is gyrated.

13. The apparatus of claim 12 wherein the display an electronic display electrically connected to the sensor to display information on an internal angle of gyration of the mold.

14. The apparatus of claim 12 wherein the sensor comprises at least one sensor operative to sense an end of the material in the mold, and at least one other sensor operative to sense a position of the mold cylinder.

15. The apparatus of claim 12 further comprising at least one mold plate within the mold cylinder, and at least one sensor operative to sense a position of the mold plate within the mold cylinder.

16. The apparatus of claim 12 wherein the sensor comprises an array of sensors operative to sense a surface or end of the material in the mold, and an array of sensors operative to sense a position of the mold cylinder.

17. The apparatus of claim 16 wherein the array of sensors is a radial array.

18. The apparatus of claim 12 further comprising a first mold plate within the mold cylinder in contact with material in the mold, and a second mold plate within the mold cylinder in contact with material in the mold, at least one sensor operative to sense a position of the first mold plate, and at least one additional sensor operative to sense a position of the second mold plate, and at least one mold position sensor operative to sense a position of the mold cylinder.

19. The apparatus of claim 18 further comprising an array of three sensors operative to sense a position of the first mold plate or second mold plate, and an array of three sensors operative to sense a position of the mold cylinder.

20. The apparatus of claim 12 wherein the sensor operative to sense an internal angle of gyration of the mold comprises a housing located within the mold, the housing having a surface parallel to a surface of material in the mold and at least one sensor connected to the housing.

21. A gyratory compactor for compacting a material specimen in a mold while the mold is gyrated, the gyratory compactor comprising:
   a mold for holding a material specimen;
   means for compacting the material specimen in the mold;
   means for gyrating the mold while the material specimen is compacted in the mold, and
   sensing means for sensing an angle of gyration of the mold, and
   means for presenting information on an internal angle of gyration of the mold during gyration of the mold by the gyratory compactor.

22. The gyratory compactor of claim 21 wherein the sensing means comprises at least one sensor located substantially within the mold and operative to sense an orientation of an end of the material in the mold relative to the mold, and at least one sensor located substantially outside of the mold for sensing a position of the mold cylinder relative to a fixed portion of the gyratory compactor.

23. The gyratory compactor of claim 21 further comprising at least one mold plate aligned with a surface of material in the mold, and wherein the sensing means comprises at least one sensor operative to sense a position or orientation of the mold plate.

24. The gyratory compactor of claim 21 wherein the sensing means comprises an array of sensors.

25. The gyratory compactor of claim 21 wherein the means for presenting information on an internal angle of gyration of the mold during gyration of the mold by the gyratory compactor comprises a display of information on an internal angle of gyration acquired from the sensing means.

26. The gyratory compactor of claim 25 wherein the display is in the form of a computer screen display.

27. The gyratory compactor of claim 26 wherein the display is in the form of a liquid crystal or light emitting diode display.

28. In a material test machine having mold for holding a material to be tested, and a plate substantially within the mold and in contact with material in the mold, an angle measurement device for measuring an angle between the plate and the mold, the angle measurement device having a housing in contact with the plate, and one or more sensors in the housing operative to sense a position of the mold cylinder relative to the plate, the sensor being operatively connected to an electronic circuit operative to produce data on an angle between the plate and the mold cylinder, and a display for displaying data on an angle between the plate and the mold cylinder.

29. A gyratory compactor comprising:
   a mold for holding a material specimen;
   a mold gyrator for gyrating the mold with a material specimen in the mold;
   a ram for applying a force to the material specimen in the mold;
   a sensor for sensing an angular orientation of an end of the material specimen relative to the mold cylinder as the mold is gyrated, and
   a display for displaying information on an angular orientation of an end of the material specimen relative to the mold cylinder as the mold is gyrated.

30. An internal gyration angle measurement and display system for use with a material test machine which has a mold for holding a material and a mechanism for gyrating the mold and compressing the material in the mold, the internal gyration angle measurement and display system comprising:
   at least one sensor which senses an angle between the material in the mold and a surface of the mold;
   at least one sensor which senses an angle between the mold and a fixed portion of the test machine, and
   a display for displaying an internal gyration angle determined from data from the sensors.

31. A method of measuring and displaying an internal angle of gyration in a gyratory compactor device having a material holding mold, which is mechanically gyrated, and at least one mold plate in contact with material in the mold, the mold plate being able to move relative to the mold cylinder as the mold is gyrated, the method comprising the steps of:
   providing a sensor which senses an angular orientation of the mold plate relative to the mold cylinder as the mold is gyrated, the sensor providing information output in the form of a display indicative of an internal angle of gyration as the mold is gyrated.

* * * * *